United States Patent [19]

Fugoso et al.

[11] Patent Number: 5,545,138
[45] Date of Patent: Aug. 13, 1996

[54] ADJUSTABLE STIFFNESS DILATATION CATHETER

[75] Inventors: Mauricio L. Fugoso, Chula Vista; Don H. Tran, Westminster, both of Calif.

[73] Assignee: Medtronic, Inc., Minneapolis, Minn.

[21] Appl. No.: 202,526

[22] Filed: Feb. 28, 1994

[51] Int. Cl.$^6$ .................... A61M 29/00; A61M 25/00
[52] U.S. Cl. .................. 604/102; 604/282; 606/192
[58] Field of Search ............... 604/96–103, 280, 604/282; 606/192–196; 600/18

[56] References Cited

U.S. PATENT DOCUMENTS

| | | | |
|---|---|---|---|
| 3,402,717 | 9/1968 | Doherty | 604/99 X |
| 3,834,394 | 9/1974 | Hunter et al. | 604/99 X |
| 3,985,139 | 10/1976 | Penar | 604/99 |
| 4,597,755 | 7/1986 | Samson et al. | 604/96 |
| 4,655,746 | 4/1987 | Daniels et al. | 604/53 |
| 4,748,982 | 6/1988 | Horzewski et al. | |
| 4,762,129 | 8/1988 | Bonzel | 604/194 |
| 4,771,777 | 9/1988 | Horzewski et al. | 604/102 X |
| 4,884,573 | 12/1989 | Wijay et al. | 606/194 |
| 4,927,413 | 5/1990 | Hess | 604/95 |
| 4,968,300 | 11/1990 | Moutafis et al. | 604/96 |
| 4,998,923 | 3/1991 | Samson et al. | 606/194 |
| 5,021,045 | 6/1991 | Buckberg et al. | 604/53 |
| 5,171,222 | 12/1992 | Euteneuer et al. | 604/102 |
| 5,176,637 | 1/1993 | Sagae | 604/96 |
| 5,180,367 | 1/1993 | Kontos et al. | 604/101 |
| 5,203,338 | 4/1993 | Jang | 128/662.06 |
| 5,232,445 | 8/1993 | Bonzel | 604/96 |
| 5,232,446 | 8/1993 | Arney | 604/96 |
| 5,242,396 | 9/1993 | Evard | 604/96 |
| 5,279,562 | 1/1994 | Sirhan et al. | 604/96 |
| 5,300,025 | 4/1994 | Wantink | 604/96 |
| 5,318,527 | 6/1994 | Hyde et al. | 604/95 |
| 5,328,472 | 7/1994 | Steinke et al. | 604/102 |

FOREIGN PATENT DOCUMENTS

9217236  10/1992  WIPO.

*Primary Examiner*—John D. Yasko
*Assistant Examiner*—Adam J. Cermak
*Attorney, Agent, or Firm*—Dianne M. F. Plunkett; Harold R. Patton

[57] ABSTRACT

A catheter with a guidewire shaft (1) with a proximal end which is free to move, the proximal end of the catheter having either a dual lumen (14) embodiment or a single lumen (6) embodiment. The dual lumen (14) embodiment has a stiffening wire lumen (17) through which a stiffening wire (12) extends and an inflation lumen (16) which is in fluid communication with the balloon (3). The single lumen (6) embodiment has a stiffening wire lumen (21) through which the stiffening wire (20) extends with the stiffening wire (20) defining an inflation lumen (22) which is in fluid communication with the balloon (3). A method of changing the stiffness of the distal end of a catheter is disclosed including, placing a stiffening wire (12) in an inflation lumen (5) or placing a stiffening wire (20) in a stiffening wire lumen (21) and advancing the stiffening wire up to the proximal end of the balloon (3) and stopping when the desired level of stiffness is achieved.

8 Claims, 5 Drawing Sheets

ADJUSTABLE STIFFNESS DILATATION CATHETER

FIELD OF THE INVENTION

The present invention relates to balloon dilatation catheters, and more particularly, to adjustable stiffness exchange catheters.

BACKGROUND OF THE INVENTION

Catheters comprise tube-like members inserted into the body for diagnostic or therapeutic medical reasons. One of the therapeutic procedures applicable to the present invention is known as percutaneous transluminal coronary angioplasty (PTCA). The first PTCA procedure was developed in approximately 1976–1977 by Dr. Andreas Gruntzig. This fixed wire system featured a core or guidewire fixed within the catheter to stiffen it so that it could be pushed into position in the vascular system. Blockage in a coronary artery could be reduced by positioning the balloon dilatation catheter across from the blockage and inflating the balloon causing the blockage to decrease.

If a catheter must be exchanged for one of a different size, an over-the-wire system is advantageous because the guidewire can be left in place. The catheter is withdrawn over the guidewire and another catheter slid into place over it. A disadvantage of this exchange procedure is that it is difficult to keep the guidewire in place, since removing the catheter requires removal of the guidewire and subsequent recrossing of the stenosis. Alternatively a very long "exchange" guidewire of approximately 300 cm can be used. This is difficult to handle because such a procedure requires two operators who must be in communication during the procedure. This requires more time and risks contamination by dropping the guidewire from the sterile field. An alternative to these long exchange guidewires is a two-part guidewire. This is also undesirable because it requires additional time to assemble and may be too thick to allow smooth exchanges.

Rapid exchange catheters were developed to respond to the disadvantage of the long "change" wire in over-the-wire systems. These catheters have shorter guidewire lumens passing through the balloon so that the guidewire exits from the catheter closer to the balloon than to the proximal end of the catheter. This enables the physician to anchor or hold the guidewire as he or she removes the catheter from the body with the exchange occurring over the shorter guidewire lumen. Various systems of rapid exchange catheters have been developed as follows.

U.S. Pat. No. 4,597,755, to Samson, et al., for "Large Bore Catheter Having Flexible Tip Construction" discloses "[a] balloon flushing wire or tube 46 . . . mounted in the side arm 43 and extends through the passage 38 into the distal extremity of the balloon 37 . . . ". See col. 3, lines 26–28. ". . . [A]ll the air within the balloon is forced out through the balloon flushing tube or wire 46." See col. 3, lines 43–45".

U.S. Pat. No. 4,748,982 to Horzewski, et al., "Reinforced Balloon Dilatation Catheter with Slitted Exchange Sleeve and Method" discloses a short guidewire lumen entering proximal to the balloon and exiting at the distal end of the balloon.

U.S. Pat. No. 4,762,129 to Bonzel and continuation U.S. Pat. No. 5,232,445, for "Dilatation Catheter" was one of the first rapid exchange catheters. It discloses a "first tube having sufficient stiffness that the second tube and expandable balloon can readily be advanced . . . along the guide wire by exerting a pushing . . . force upon the first tube, in combination with the elongated guide wire." See col. 4, lines 6–11.

U.S. Pat. No. 4,927,413 to Hess, for "Catheter for Balloon Angioplasty" discloses a ". . . core means 20a (which is) withdrawn or advanced to vary the shaft stiffness . . . " see col. 5, lines 65–67. "It is understood that shaft 12 is sealed with respect to passage 18, such as by use of a plastic covering, so that balloon 34 may be inflated." See col. 4, lines 41–43 and FIG. 4.

U.S. Pat. No. 4,968,300 to Moutafis, et al., for "Balloon Stretch Mechanism" discloses a support member 103 extending through the balloon.

U.S. Pat. No. 5,180,367 to Kontos, et al., for "Procedure and Balloon Catheter System for Relieving Arterial or Veinal Restrictions Without Exchanging Balloon Catheters" discloses a short guidewire lumen running either through the balloon as in FIG. 3 or running along the outside of the balloon as in FIG. 5.

WO Patent 92/17236 to Scopton, et al., for "Adjustably Stiffenable Convertible Catheter Assembly" discloses a convertible-type balloon catheter having at least three lumens. The first lumen accommodates the stiffening mandrel. The second lumen is the inflation lumen and the third lumen functions as a lumen for an over-the-wire mode and a rapid exchange mode, using part of the lumen for a guidewire and part of that lumen for catheter stiffening assistance.

SUMMARY OF THE INVENTION

The objects of the invention are to create a dilatation catheter rapid exchange system over a guidewire, to provide a proximal end which can change stiffness for enhanced pushability and trackability, and to decrease time during the inflation or deflation of the balloon. The features and advantages of the present invention, as well as others, are accomplished by providing a catheter with a guidewire shaft with a proximal end which is optionally free to move, the proximal end of the catheter having either a dual lumen embodiment or a single lumen embodiment. The dual lumen embodiment has a stiffening wire lumen through which a stiffening wire extends and an inflation lumen which is in fluid communication with the balloon. The single lumen embodiment has a stiffening wire lumen through which the stiffening wire extends with the stiffening wire defining an inflation lumen which is in fluid communication with the balloon. A method of changing the stiffness of the distal end of a catheter is disclosed including placing a stiffening wire in an inflation lumen or a stiffening wire lumen and advancing the stiffening wire no farther then the proximal end of the balloon and stopping when the desired level of stiffness is achieved.

DETAILED DESCRIPTION OF THE PREFERRED EMBODIMENTS

Figure 1:
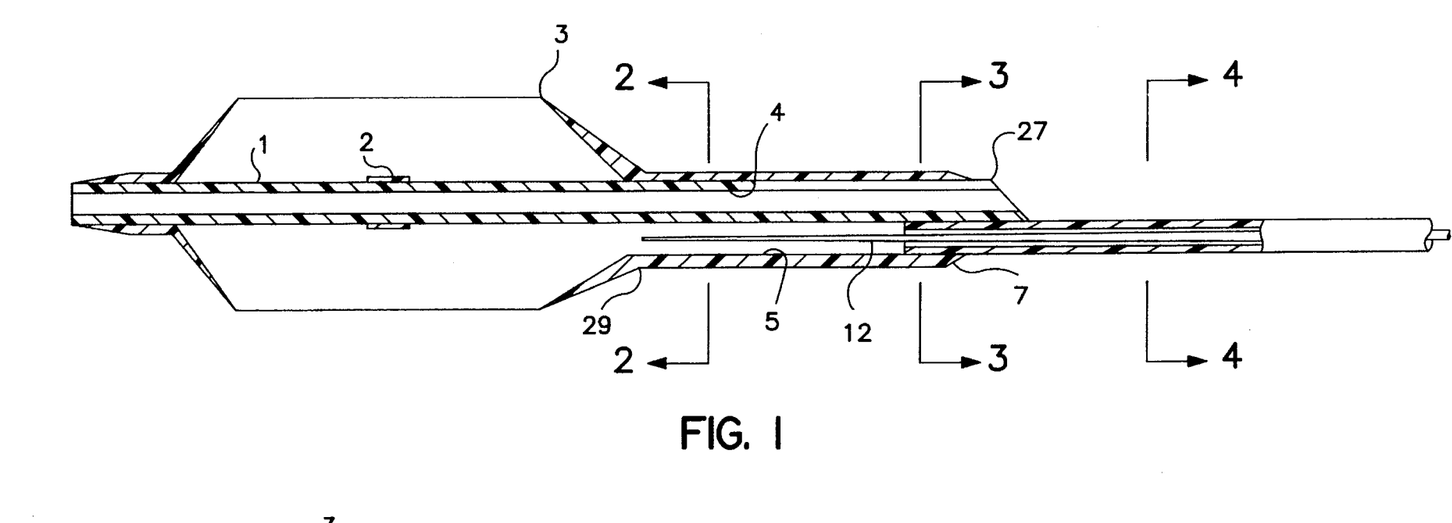
FIG. 1 is a longitudinal cross-sectional view of the distal portion of the invention.
Figures 6, 7:
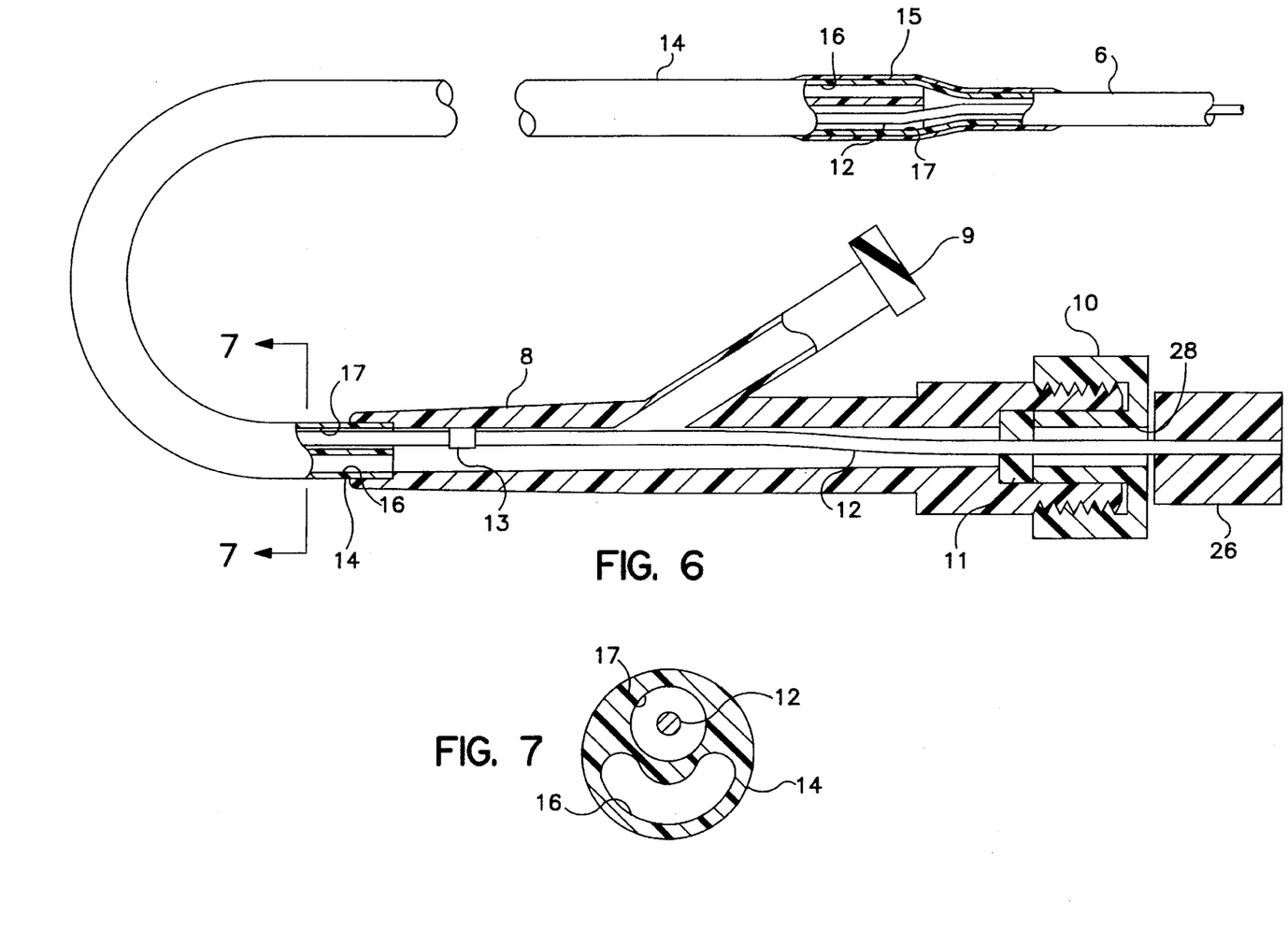
FIG. 6 is a cut-away longitudinal cross-sectional view of the proximal portion of the invention of the first embodiment.
FIG. 7 is a cross-sectional view taken along the line 7—7 of FIG. 6.
Figure 8:
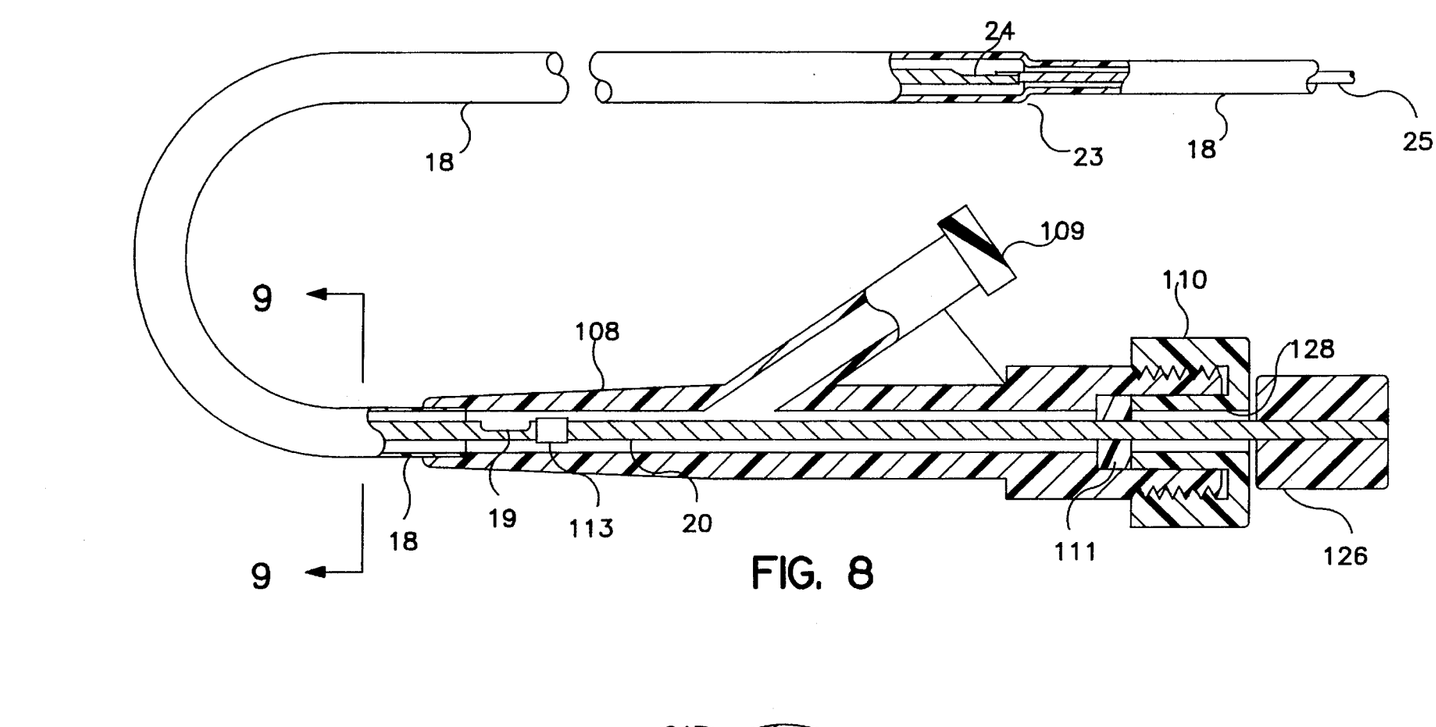
FIG. 8 is a cut-away longitudinal cross-sectional view of the proximal portion of the 2nd embodiment.

Applicant's catheter has two embodiments. These embodiments have a common distal portion with differing proximal portions. FIG. 1 shows the common distal portion for the two embodiments. FIG. 6 shows the first embodiment of the proximal portion and has a dual lumen shaft. FIG. 8 shows the second embodiment of the proximal portion but has a single lumen shaft.

In FIG. 1, which depicts the common distal portion which includes a balloon (3) and guidewire lumen shaft (1) defining a guidewire lumen (4) having an exit port (130). The balloon (3) may be of 20 mm–40 mm in length, for example, although those skilled in the art will recognize that other sizes are suitable. The guidewire lumen shaft (1) has a length of approximately 7 cm and an inside diameter that can be made compatible with a desired guidewire size. The guidewire lumen shaft (1) has an outside diameter of approximately 0.058 cm (0.023 inches). A suitable material for the guidewire shaft (1) is high density polyethylene (HDPE).

A radiopaque material in hollow cylindrical form is bonded to the guidewire lumen shaft (1) preferably in the mid-section of the balloon (3) to form a radiopaque marker band (2). The radiopaque marker band (2) could be located other places such as the proximal and/or distal ends of the balloon (3). The marker band (2) is used to provide a fluoroscopic indication of the location of the balloon (3) thereby allowing the operator to adjust the position of the balloon (3). Preferred materials for the marker band (2) include 100% gold, 100 % iridium, or alloys of these materials such as a Pt-Ir alloy consisting of 90% platinum and 10% iridium. The preferred density is of at least 19.3 to 21.0 gm/cm$^3$.

Figure 2:
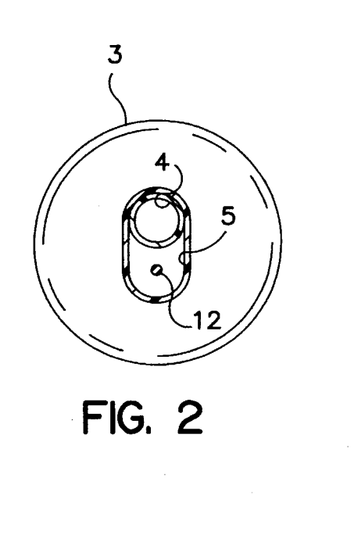
FIG. 2 is a cross-sectional view taken along the line 2—2 of FIG. 1.
Figure 3:
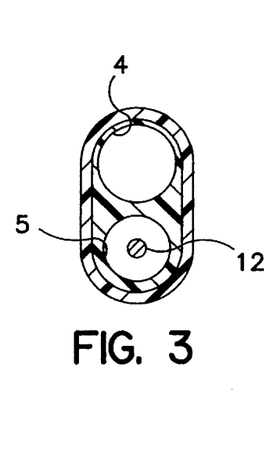
FIG. 3 is a cross-sectional view taken along the line 3—3 of FIG. 1.
Figure 4:
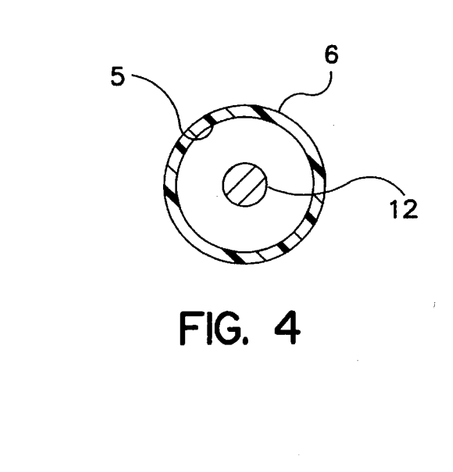
FIG. 4 is a cross-sectional view taken along the line 4—4 of FIG. 1.
Figure 5:
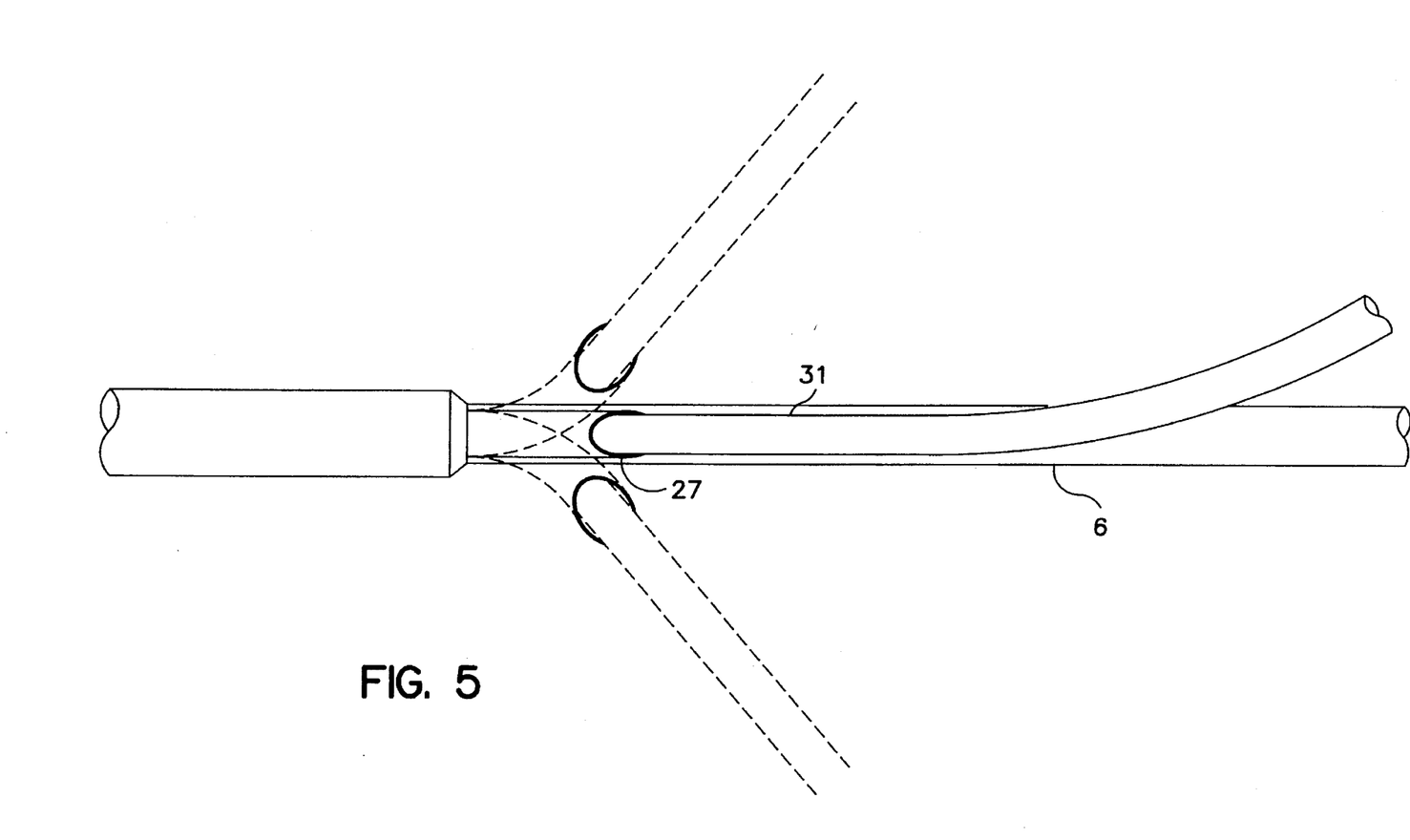
FIG. 5 is a top elevational view of FIG. 1 guidewire entry port.

The distal end of the guidewire lumen shaft (1) is heat bonded to the distal end of balloon (3) for a length of 3–5 mm and positioned so that the radiopaque marker band (2) is at the inside mid-section of the balloon (3). The balloon (3) proximal portion is heat formed to have a cross-section per FIG. 2. This heat forming creates the balloon inflation/deflation lumen (5). FIG. 3 is a cross-sectional view after heat bonding the single lumen shaft (6) of FIG. 6 parallel with the proximal portion of the guidewire lumen (1) and balloon proximal end as per FIG. 1. The single lumen shaft (6) can be made preferably of high density polyethylene material. Excess balloon material is trimmed to a tapered end (7). The guidewire lumen proximal end (27) extends about 2 mm to 4 mm beyond the balloon tapered end (7) in the proximal direction and is cut at about 45 degrees. The 2 mm to 4 mm guidewire lumen proximal end (27) is not heat bonded to the shaft (6) as the balance of the guidewire (1) lumen is, and thus is free to move in different directions to aid the distal portion of the dilatation catheter in following the guidewire during withdrawal or exchange. Refer to FIG. 5. Although the guidewire lumen proximal end (27) could be affixed to the shaft (6), not doing so is preferred because the ability of the guidewire lumen proximal end (27) to move reduces guidewire (31) kinking or binding.

FIGS. 6 and 8 represent the two embodiments of the proximal portion of the invention which share the common FIG. 1 distal portion. The proximal end of FIG. 1 is continuous with either the distal end of FIG. 6 or the distal end of FIG. 8. Each of the two embodiments contain a stiffening wire, used to vary the stiffness of the catheter distal end, and without which, the catheter cannot be readily advanced.

The first embodiment of the proximal portion contains a dual lumen shaft (14) and is represented in FIG. 6. which shows a cutaway longitudinal cross-sectional view. This includes a molded Y-manifold (8), the dual lumen shaft (14) of a material such as HDPE or nylon. The dual lumen shaft (14) defines the inflation lumen (16) and the stiffening wire lumen (17). A solid round stiffening wire (12) is slidably received in the stiffening wire lumen (17), the stiffening wire (12) having a tapered distal end (12) of FIG. 1, a stopper (13) brazed approximately 4 cm distal to the holder (26) which is bonded to the proximal end. The distal end of the stiffening wire (12) is positioned per FIG. 1, ending proximal to the balloon cone (29). The stiffening wire is made of solid round stainless steel of approximately 0.036 cm (0.014 inches) in diameter, with a length of approximately 110 cm followed by a tapered distal portion of approximately 27 cm.

Also depicted in FIG. 6 is a longitudinal cross-sectional view of a lap joint (15) coupling sleeve located between the dual lumen shaft (14) and the single lumen shaft (6). The single lumen shaft can be made of a material such as HDPE. The joint lap (15) coupling sleeve can be made of a material such as low density polyethylene (LDPE). The dual lumen shaft (14) can be formed in a variety of ways including a mold utilizing two mandrels. The lap joint (15) coupling sleeve is heat shrunk about the distal end of the dual lumen shaft (14) and the proximal end of the single lumen shaft (6) which have been placed end to end. The lap joint (15) allows the single lumen shaft (6) and the dual lumen shaft (14) to be in fluid communication. The stiffening wire (12) can then be slid from the dual lumen shaft (14) into the single lumen shaft (6). The inflation lumen (16) and the stiffening wire lumen (17) are now one lumen in the single lumen shaft (6). The single lumen shaft (6) now is in effect a balloon inflation shaft. The decreased diameter of the single lumen shaft (6) when compared to the dual lumen shaft (14) is advantageous for maintaining a low profile when the distal end of the single lumen shaft is affixed to the guidewire shaft (1) and encircled by the balloon (3).

The molded Y-manifold (8) of FIG. 6 is integrally attached to the proximal end of the dual lumen shaft (14), and serves to allow fluid communication between the inflation lumen (16) and the inflation/deflation port (9). A luer fitting (9) comprises the inflation/deflation port. A Tuohy-Borst adapter is attached to the proximal end of the manifold (8) which serves as the stiffening wire port (28). This Tuohy-Borst adapter has a rotating knob (10) used to seal and unseal the stiffening wire (12) by compressing and decompressing silicone material (11).

The second embodiment of the proximal portion of the catheter contains a single lumen shaft (18) and is represented in FIG. 8. The advantages of the single lumen embodiment over the dual lumen embodiment include a smaller profile, simpler assembly and fabrication, improved inflation/deflation times and a significant increase in proximal stiffness due to a larger diameter stiffening wire (20) which can be made of stainless steel.

The FIG. 8 single lumen embodiment has a step-down (23) in the single lumen shaft (18) at the distal end of the stiffening wire (20). Step-down (23) is about 3 cm to 5 cm from the guidewire lumen proximal end (27) of FIG. 1 and most preferable 3 cm. This is advantageous for maintaining a low profile when the distal end of the single lumen shaft is affixed to the guidewire shaft (1) and encircled by the balloon (3). The distance between the inner diameter and the outer diameter of the single lumen shaft (18) remain the same after the step down (23) as before the step down (23). Those skilled in the art will recognize that a step down (23) can be created in a variety of ways, as for example necking it down to a smaller diameter with a heating process.

Figure 9:
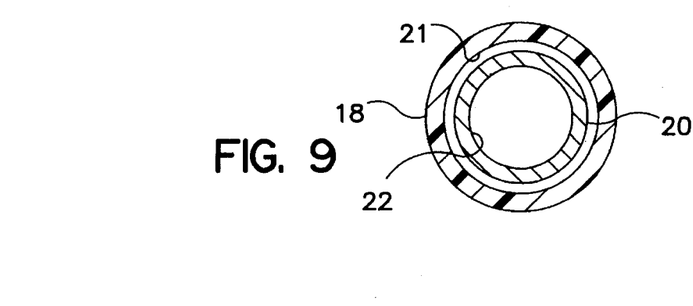
FIG. 9 is a cross-sectional view taken along line 9—9 of FIG. 8.

When the distal end of FIG. 8 is heat bonded to the proximal end of FIG. 1 the stiffening wire (12) of FIG. 1 becomes the FIG. 8 tapered round wire (25) extending through the single lumen shaft (18). FIG. 9 represents a cross-sectional view along the line 9—9 of FIG. 8 showing a stiffening wire lumen (21) and an inflation/deflation lumen (22).

The molded Y-manifold (108) of FIG. 8 is integrally attached to the proximal end of the single lumen shaft (20), and serves to allow fluid communication between the inflation lumen (22) and the inflation\deflation port (109). A luer fitting (109) comprises the inflation/deflation port. A Tuohy-Borst adapter is attached to the proximal end of the manifold (108) which serves as the stiffening wire port (128). This Tuohy-Borst adapter has a rotating knob (110) used to seal and unseal the stiffening wire (20) by compressing and decompressing silicone material (111).

Figures 10, 11, 12:
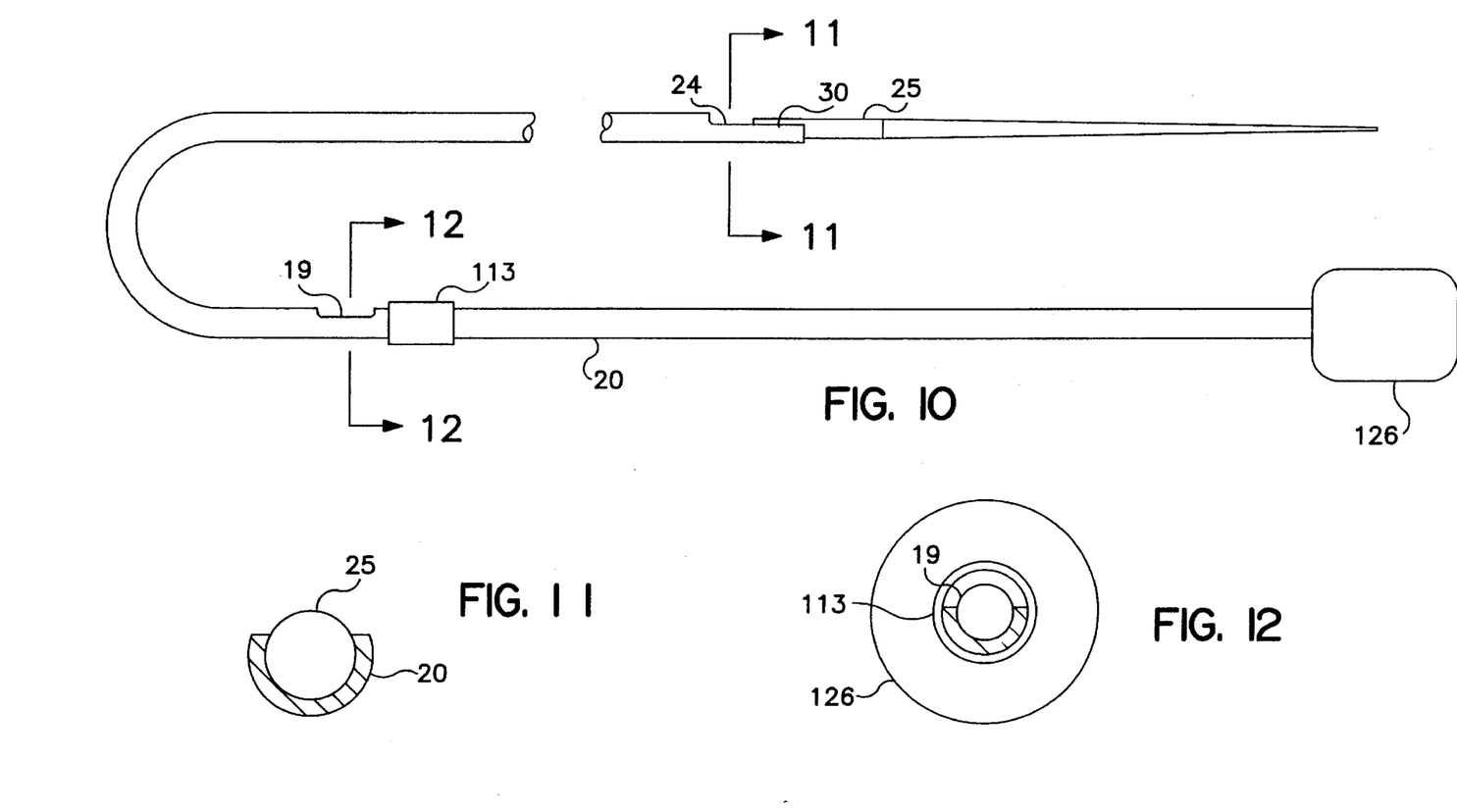
FIG. 10 is a side elevation view of the stiffening wire of FIG. 8.
FIG. 11 is a cross-sectional view taken along the line 11—11 of FIG. 10.
FIG. 12 is a cross-sectional view taken along the line 12—12 of FIG. 10.

FIG. 10 is a side elevation view of the larger diameter hollow stiffening wire (20) of the single lumen embodiment of FIG. 8. This depicts the stiffening wire (20) with a holder (126) which is bonded to the proximal end. The stiffening wire (20) is hollow, serving as an inflation lumen, and extends approximately 110 cm from the holder (126). The stiffening wire (20) has a diameter of approximately 0.058 cm (0.023 inches).

In FIG. 10 the tapered round wire (25) is solid, approximately 32 cm in length and can be made of stainless steel. Beginning at the distal end, the tapered round wire (25) has a 0.0076 cm (0.003 inch) diameter. The tapered round wire (25) tapers upward from the distal end for a length of 2 cm, at which point the diameter reaches 0.020 cm (0.008 inch). The diameter remains constant at 0.020 cm (0.008 inch) for a length of 26 cm. At 28 cm from the distal end, the diameter tapers upward for a length of 2 cm until it reaches 0.036 cm (0.014 inches) which it maintains for 2 cm.

FIGS. 8 and 10 show an opening (19) on the hollow stiffening wire (20) approximately 4 cm from the proximal end of the hollow stiffening wire (20), this serves as the inflation contrast media entry port. The stopper (113) is brazed just proximal of opening (19) and approximately 4 cm distal of holder 126. FIG. 8 and FIG. 10 show an opening (24) at the distal end of the hollow stiffening wire (20). The tapered round wire (25) is brazed at (30), 2 mm from the distal end of the hollow stiffening wire. There is also an opening (24) at the braze joint (30) which allows the inflation contrast media fluid to flow in and out. Both openings (19) and (24) are about ⅓ of the outer diameter of the stiffening wire (20) and 4 mm long.

If the user wishes to change the stiffness of the distal portion of the catheter using either the FIG. 6 dual lumen embodiment or the FIG. 8 single lumen embodiment, the user will grasp the holder (26 or 126) and pull outward until the stopper (13 or 113) reaches the distal end of silicone material (11 or 111) and stops. At this moment the distal end of the stiffening wire (12 or 25) is positioned at the proximal end of the balloon tapered end (7). This decreases the stiffness of the distal portion of catheter. The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 1 | guidewire lumen shaft |
| 2 | radiopaque marker band |
| 3 | balloon |
| 4 | guidewire lumen |
| 5 | balloon inflation lumen |
| 6 | single lumen shaft |
| 7 | balloon tapered end |
| 8 | Y-manifold |
| 9 | inflation/deflation port |
| 10 | rotating knob |
| 11 | silicone material |
| 12 | stiffening wire |
| 13 | stopper |
| 14 | dual lumen shaft |
| 15 | lap joint |
| 16 | dual lumen shaft inflation lumen |
| 17 | dual lumen shaft stiffening wire lumen |
| 18 | single lumen shaft |
| 19 | opening for fluid contrast media entry |
| 20 | larger diameter stiffening wire |
| 21 | single lumen shaft stiffening wire lumen |
| 22 | stiffening wire inflation lumen |
| 23 | step down |
| 24 | opening for fluid contrast entry/exit |
| 25 | tapered round wire |
| 26 | holder |
| 27 | guidewire lumen proximal end |
| 28 | stiffening wire port |
| 29 | balloon cone |
| 30 | braze |
| 31 | guidewire |
| 108 | Y-manifold |
| 109 | inflation/deflation port |
| 110 | rotating Knob |
| 111 | silicone material |
| 113 | stopper |
| 126 | holder |
| 128 | stiffening wire port |
|  | guidewire lumen exit port |

What is claimed is:

1. A dilatation catheter comprising:

a balloon having a distal end and a proximal end;

a balloon inflation shaft having a distal end and a proximal end, the balloon inflation shaft defining a balloon inflation lumen, the balloon inflation lumen being in fluid communication with the balloon, the proximal end of the balloon encircling and being sealingly affixed to the balloon inflation shaft;

a stiffening wire extending longitudinally through the balloon inflation shaft, the stiffening wire defining an inflation lumen in fluid communication with the balloon, the stiffening wire having a proximal end and a distal end;

the stiffening wire having a first opening distal to the proximal end of the stiffening wire, the first opening being in fluid communication with the balloon; and the stiffening wire having a second opening proximal to the distal end of the stiffening wire and distal to the first opening, the second opening being in fluid communication with the balloon.

2. A dilatation catheter comprising:

a balloon having a distal end and a proximal end;

a balloon inflation shaft having a distal end and a proximal end, the balloon inflation shaft defining a balloon inflation lumen, the balloon inflation lumen being in fluid communication with the balloon, the proximal end of the balloon encircling and being sealingly affixed to the balloon inflation shaft;

a stiffening wire extending longitudinally through the balloon inflation shaft, the stiffening wire defining an inflation lumen in fluid communication with the balloon, the stiffening wire having a proximal end and a distal end; and a wire with a proximal end and a distal end, the wire tapering down towards the distal end, the proximal end of the wire being affixed to the distal end of the stiffening wire.

3. A dilatation catheter comprising:

a balloon having a distal end and a proximal end;

a balloon inflation shaft having a distal end and a proximal end, the balloon inflation shaft defining a balloon inflation lumen, the balloon inflation lumen being in fluid communication with the balloon, the proximal end of the balloon encircling and being sealingly affixed to the balloon inflation shaft;

a stiffening wire extending longitudinally through the balloon inflation shaft, the stiffening wire defining an inflation lumen in fluid communication with the balloon, the stiffening wire having a proximal end and a distal end; and a stopper affixed to the stiffening wire distal to the proximal end of the stiffening wire.

4. A dilatation catheter comprising:

a balloon having a distal end and a proximal end;

a balloon inflation shaft having a distal end and a proximal end, the balloon inflation shaft defining a balloon inflation lumen, the balloon inflation lumen being in fluid communication with the balloon, the proximal end of the balloon encircling and being sealingly affixed to the balloon inflation shaft;

a stiffening wire extending longitudinally through the balloon inflation shaft, the stiffening wire having a proximal end and a distal end; and a wire with a proximal end and a distal end, the wire tapering down towards the distal end, the proximal end of the wire being affixed to the distal end of the stiffening wire.

5. A catheter comprising:

a balloon having a distal end and a proximal end;

a guidewire shaft, having a distal end and a proximal end, and defining a guidewire lumen, the guidewire shaft distal end defining an exit port for the guidewire lumen, the guidewire shaft proximal end being adapted for insertion into a vessel of a patient, the guidewire shaft extending longitudinally through the balloon, the distal end of the balloon being sealingly affixed to the distal end of the guidewire shaft;

a balloon inflation shaft having a distal end and a proximal end, the balloon inflation shaft defining a balloon inflation lumen, the balloon inflation lumen being in fluid communication with the balloon, the balloon inflation shaft being longer than the guidewire shaft and parallel to the guidewire shaft and affixed to the guidewire shaft at a point distal to the proximal end of the guidewire shaft, the proximal end of the guidewire shaft not being affixed to the balloon inflation shaft, the proximal end of the balloon encircling and being sealingly affixed to the guidewire shaft and to the balloon inflation shaft at a point distal to the proximal end of the guidewire shaft;

a stiffening wire extending longitudinally through the balloon inflation shaft, the stiffening wire defining an inflation lumen in fluid communication with the balloon, the stiffening wire having a proximal end and a distal end;

the stiffening wire having a first opening distal to the proximal end of the stiffening wire, the first opening being in fluid communication with the balloon;

the stiffening wire having a second opening proximal to the distal end of the stiffening wire and distal to the first opening, the second opening being in fluid communication with the balloon;

a wire with a proximal end and a distal end, the wire tapering down towards the distal end, the proximal end of the wire being affixed to the distal end of the stiffening wire; and a stopper affixed to the stiffening wire distal to the proximal end of the stiffening wire.

6. A catheter according to claim 5 further comprising:

a step down in the balloon inflation shaft at the distal end of the stiffening wire; and the balloon inflation shaft having an inner diameter and an outer diameter, the inner diameter being smaller distal to the step down, the outer diameter being smaller distal to the step down while the distance between the outer diameter and inner diameter remains constant.

7. A catheter comprising:

a balloon having a distal end and a proximal end;

a guidewire shaft, having a distal end and a proximal end, and defining a guidewire lumen, the guidewire shaft distal end defining an exit port for the guidewire lumen, the guidewire shaft proximal end being adapted for insertion into a vessel of a patient, the guidewire shaft extending longitudinally through the balloon, the distal end of the balloon being sealingly affixed to the distal end of the guidewire shaft;

a balloon inflation shaft having a distal end and a proximal end, the balloon inflation shaft defining a balloon inflation lumen, the balloon inflation lumen being in fluid communication with the balloon, the balloon inflation shaft being longer than the guidewire shaft and parallel to the guidewire shaft and affixed to the guidewire shaft at a point distal to the proximal end of the guidewire shaft, the proximal end of the guidewire shaft not being affixed to the balloon inflation shaft, the proximal end of the balloon encircling and being sealingly affixed to the guidewire shaft and to the balloon inflation shaft at a point distal to the proximal end of the guidewire shaft; and wherein the proximal end of the guidewire shaft ends about 2 mm to 4 mm proximal to the distal end of the balloon inflation shaft.

8. A catheter comprising:

a balloon having a distal end and a proximal end;

a guidewire shaft, having a distal end and a proximal end, and defining a guidewire lumen, the guidewire shaft distal end defining an exit port for the guidewire lumen, the guidewire shaft proximal end being adapted for insertion into a vessel of a patient, the guidewire shaft extending longitudinally through the balloon, the distal end of the balloon being sealingly affixed to the distal end of the guidewire shaft;

a balloon inflation shaft having a distal end and a proximal end, the balloon inflation shaft defining a balloon inflation lumen, the balloon inflation lumen being in fluid communication with the balloon, the balloon inflation shaft being longer than the guidewire shaft and parallel to the guidewire shaft and affixed to the guidewire shaft at a point distal to the proximal end of the guidewire shaft, the proximal end of the guidewire shaft not being affixed to the balloon inflation shaft, the proximal end of the balloon encircling and being sealingly affixed to the guidewire shaft and to the balloon inflation shaft at a point distal to the proximal end of the guidewire shaft; and wherein the proximal end of the guidewire shaft ends closer to the proximal end of the balloon then to the proximal end of the balloon inflation shaft.

* * * * *